US006908196B2

(12) United States Patent
Herekar et al.

(10) Patent No.: US 6,908,196 B2
(45) Date of Patent: Jun. 21, 2005

(54) SYSTEM AND METHOD FOR PERFORMING OPTICAL CORRECTIVE PROCEDURES WITH REAL-TIME FEEDBACK

(75) Inventors: Satish Venkatesh Herekar, Palo Alto, CA (US); Daniel R. Neal, Tijeras, NM (US); Richard James Copland, Albuquerque, NM (US); David Neal, Albuquerque, NM (US)

(73) Assignee: WaveFront Sciences, Inc., Albuquerque, NM (US)

( * ) Notice: Subject to any disclaimer, the term of this patent is extended or adjusted under 35 U.S.C. 154(b) by 124 days.

(21) Appl. No.: 10/369,513

(22) Filed: Feb. 21, 2003

(65) Prior Publication Data

US 2003/0174281 A1 Sep. 18, 2003

Related U.S. Application Data

(63) Continuation of application No. PCT/US02/35076, filed on Nov. 1, 2002, and a continuation-in-part of application No. 09/692,483, filed on Oct. 20, 2000, now Pat. No. 6,550,917.
(60) Provisional application No. 60/331,196, filed on Nov. 9, 2001.

(51) Int. Cl.[7] ................................................ A61B 3/10
(52) U.S. Cl. ........................................................ 351/221
(58) Field of Search ................................. 351/211, 212, 351/220, 221; 606/4, 5

(56) References Cited

U.S. PATENT DOCUMENTS

| 4,881,808 | A | * | 11/1989 | Bille et al. ................... 351/221 |
| 5,571,107 | A | | 11/1996 | Shaibani et al. |
| 5,828,454 | A | | 10/1998 | Gust |
| 5,906,608 | A | | 5/1999 | Sumiya et al. |
| 6,086,204 | A | * | 7/2000 | Magnante ................... 351/212 |
| 6,099,522 | A | | 8/2000 | Knopp et al. |
| 6,271,914 | B1 | | 8/2001 | Frey et al. |
| 6,271,915 | B1 | | 8/2001 | Frey et al. |

* cited by examiner

Primary Examiner—George Manuel

(57) ABSTRACT

A real-time refractory control system includes a laser refractive surgery instrument for modifying the refraction of the eye, an objective diagnostic apparatus for measuring the refraction and aberrations of the eye, and an aperture-sharing element to inject a refractive surgery beam and a monitoring diagnostic beam. An associated method of adjusting a refraction of an eye, includes: performing a procedure to modify the refraction of the eye; while the procedure is being performed, measuring the refraction and/or an aberration of the eye; and terminating the procedure when a change in the measured refraction and/or the measured aberration reaches a desired value.

14 Claims, 5 Drawing Sheets

SYSTEM AND METHOD FOR PERFORMING OPTICAL CORRECTIVE PROCEDURES WITH REAL-TIME FEEDBACK

This application is a continuation of International Patent Application PCT/US02/35076, filed on 1 Nov. 2002, claiming the priority benefit under 35 U.S.C. § 119(e) from U.S. Provisional Application No. 60/331,196, filed on 9 Nov. 2001, the entire contents of each of which are hereby incorporated by reference in their entirety for all purposes as if fully set for the herein. This application is also a Continuation-in-Part of U.S. patent application Ser. No. 09/692,483, filed on 20 Oct. 2000 now U.S. Pat. No. 6,550,917, in the names of inventors Daniel R. Neal, Darrell J. Armstrong, Daniel M. Topa and Richard J. Copland, entitled "Dynamic Range Extension Techniques for a Shack-Hartman Sensor Including Use in Ophthalmic Measurement" the entire contents of each of which are hereby incorporated by reference in their entirety for all purposes as if fully set for the herein.

BACKGROUND AND SUMMARY OF THE INVENTION

1. Field of the Invention

This invention pertains to the field of optical corrective surgery and more particularly to a system and method for monitoring aberrations of the eye in real time during optical corrective procedures that operate such as to leave the optical zone of the eye unobscured during the procedure.

2. Description

Several technologies have recently be developed for laser corneal surgery for correction of refractive error. These include Laser in-situ Keratotomy (Lasik), Photo-refractive Keratotomy (PRK), Redial Keratotomy, laser thermal keratotomy (LTK), and Laser Thermal Drying (LTD). These technologies use a laser either to remove material or to modify the structure of other properties of the cornea in order to make the desired changes in refraction. In the case of Lasik, a small flap of corneal material is cut and peeled back to allow ablation of the underlying material, rather than the outer epithelial layer. PRK directly ablates this outer layer. LTK and LTD apply an infrared laser to the outer periphery (outside the optical zone) to change the structure and shape of the cornea to achieve the desired refractive correction.

In each of these different technologies, the hydration state of the eye, the healing response of the particular subject, the bio-mechanics of the retina and many other factors directly contribute to the results. Furthermore, the refraction must be achieved through a pre-computed process that accounts for all of the various factors. The goal is to provide a process that achieves the desired change of refraction while minimizing the optical aberrations of the ocular system. However, in many cases the refractive surgery itself introduces significant aberrations. This may be due to either a change in the bio-mechanical structure, or merely due to the edge of the treatment zone.

A number of instruments have been developed that have served as diagnostics on this process. These includes subjective and auto-refraction, corneal topography, pachymetry, and wavefront aberrometry. Of these, only wavefront aberrometry directly measures the optical aberrations of the full optical system. Pre and post diagnostics using these advanced instruments have provided a tremendous amount of information that has lead to the improvement of the various methods.

However, there are still variables that cannot be properly monitored that affect the outcome. In particular, factors like the hydration state of the eye and healing response are difficult to account for in advance. The ablation profile for Lasik has long been known to be non-linear and have a different strength for positive or negative corrections. The ablation algorithms have been developed to take this into account, but there is still considerable variation from subject to subject because of unknown factors.

If the diagnostics could be applied in real time, during the refractive surgery, then some of this variation could be removed. This would allow the laser surgery to operate in a "closed-loop" mode, with the amount of refractive modification being monitored and controlled during the procedure. While it is possible to monitor the change in shape of the cornea in "real-time" with corneal topography or other surface means, this only indirectly affects the total optical path and hence the refraction and higher order terms.

Accordingly, it would be desirable to provide a system and method for monitoring the aberrations of the eye in real time during Laser Thermal Keratotomy, Laser Thermal Drying and other laser ablation refractive surgery procedures that operate such as to leave the optical zone unobscured. It would also be desirable to provide a system and method for using wavefront aberrometry to monitor the refractive surgery process in real time to give a signal that allows for "end-point" detection, i.e., to provide a real-time signal to the laser system to stop the procedure when the desired correction has been achieved. It would further be desirable to develop a set of nomograms for each individual aberrations, which may be described by Zernike polynomials, so that the laser profile or procedure can be adjusted in real-time to minimize the induced aberrations.

With LTK and LTD the optical zone is itself not directly modified and the refractive operation of the eye remains functional during the treatment. Thus it is possible to incorporate the diagnostics directly into the laser refractive system without obscuration or unanticipated modification of the optical zone. Wavefront aberrometry provides the added benefit of being able to monitor the effect of the refractive surgery on both the desired refraction terms (focus and astigmatism) along with various high order aberrations. Since these procedures operate near the edge of the optical zone, it is important to consider these effects. Furthermore, wavefront aberrometry directly monitors the total optical aberrations of the full system.

It should be noted, however, that there is a significant difficulty with incorporating the diagnostics into the lasers that are used for Lasik or PRK. In the case of Lasik, a cut is made through the cornea and the loose flap of corneal tissue is pulled away so the Lasik laser can ablate the underlying tissue. This means that the measurement made by any diagnostic instrument during the ablation would not be measuring the actual optical path that will result when the corneal flap is folded back down. Also, the cutting of the cornea releases the tension in the corneal fibers and that tension is not restored when the flap is laid back down. So the resulting optical performance of the cornea is not what is was before the cut was made. While it may be possible to calibrate for these effects, it certainly falls short of the goal of directly measuring the desired result in real-time during the procedure.

Frey, Burkhalter, Zepkin, Poppeliers and Campin in U.S. Pat. Nos. 6,271,914 and 6,271,915 introduced a method for ablating corneal material while monitoring the process in real time using a Hartmann plate sensor. Unfortunately, their techniques rely on modifying directly the optical zone that is measured. During the Lasik or PRK procedures that use ablation of portions of the cornea, the process of ablating material leads to unknown and undetermined optical scattering and effects during the ablation process. The surface of a dry cornea (needed for properly controlled ablation) or the interior surface that is exposed during the Lasik procedure are inherently rough. Thus these surfaces would scatter the injected and reflected light that is used for monitoring the wavefront. This significantly degrades the quality of the information obtained, making the aim difficult to achieve.

However, there are certain types of laser systems that do not directly modify the optical zone so as to affect the measurement. These include the Laser Thermal Keratotomy, Laser Thermal Drying, and femto-second laser systems. With these systems it is possible to implement a method for monitoring and controlling the optical refraction in real-time through the use of this invention.

The present invention comprises a system and method for performing optical corrective procedures with real-time feedback.

In one aspect of the invention, a system for adjusting an optical characteristic of an eye includes a refractive surgery instrument adapted to perform a procedure to modify refraction of an eye, an objective diagnostic apparatus adapted to measure at least one of the refraction of the eye and an aberration of the eye while the procedure is being performed, and an aperture-sharing element adapted to inject a refractive surgery beam and a monitoring diagnostic beam into the eye.

In another aspect of the invention, a method of adjusting a refraction of an eye, includes: performing a procedure to modify the refraction of the eye; while the procedure is being performed, measuring the refraction and/or an aberration of the eye; and terminating the procedure when a change in the measured refraction and/or the measured aberration reaches a desired value.

DETAILED DESCRIPTION

Embodiments and other aspects of the invention described herein, including the system embodiments described below, may be made or used in conjunction with inventions described, in whole or in part, in co-pending U.S. patent application Ser. No. 09/692,483 filed on 20 Oct. 2000 in the name of inventors Daniel R. Neal, Darrell J. Armstrong, Daniel M. Topa and Richard J. Copland, entitled "Dynamic Range Extension Techniques for a Shack-Hartman Sensor Including Use in Ophthalmic Measurement."

Figure 1:
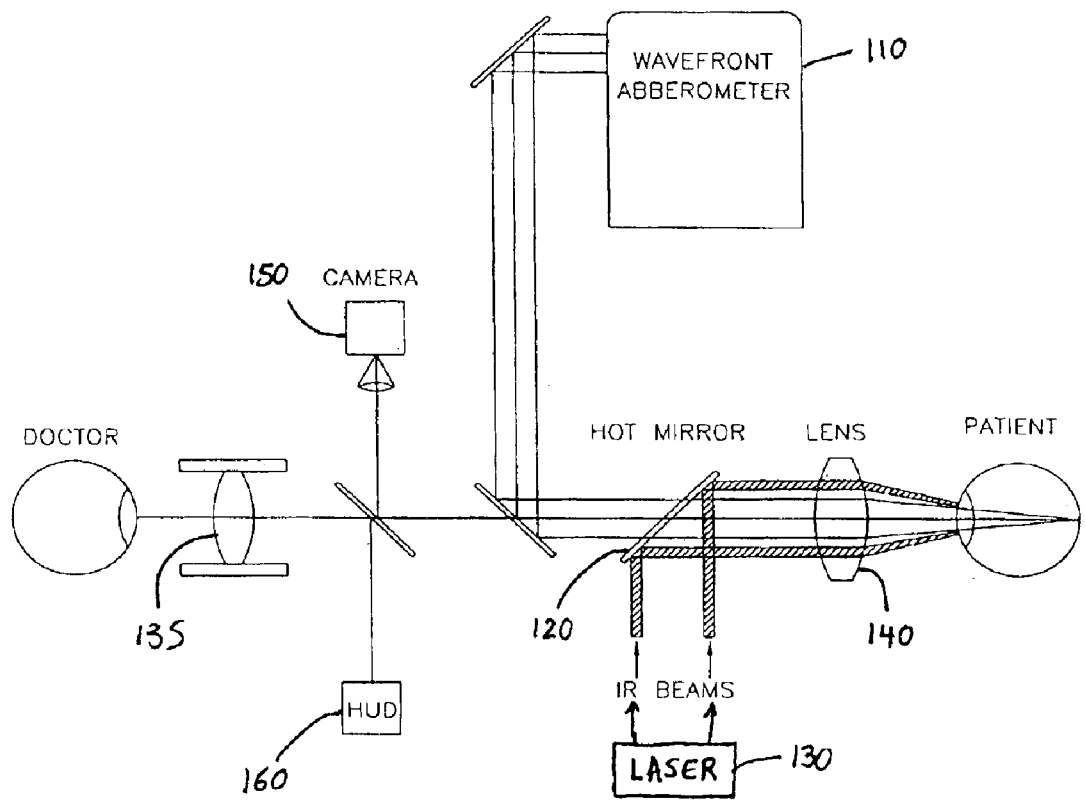
FIG. 1 is a functional diagram of one embodiment of a laser treatment system including a laser refractive surgery instrument and an objective aberrometer.

FIG. 1 shows a functional diagram of an embodiment of an integrated laser treatment system 100, comprising a laser refractive surgery instrument that is integrated with a wavefront aberrometry system. The system 100 includes a wavefront aberrometer 110, a laser 130, an aperture-sharing element 120, first and second lenses 135, 140 operating as a microscope, a camera 150, and a heads-up display (HUD) 160.

The wavefront aberrometer 110 operates by injecting a beam or pattern near the center of the pupil and then recording and monitoring the resulting light that is scattered from the retina. Beneficially, the wavefront aberrometer 110 includes a target for the patient's eye. The wavefront aberrometer 110 is arranged to monitor the central part of the optical zone. The wavefront aberrometer 110 may be a Hartmann-Shack sensor, scanning refractometer, Tscheming aberrometer or other aberrometer system.

The wavefront aberrometer 110 operates with the aperture-sharing element 120 to simultaneously inject the refractive laser beam(s) from the laser 130. Beneficially, the aperture-sharing element may comprise a dichroic mirror that passes visible light (and a scanning beam from the wavefront aberrometer 110) straight through while reflecting infrared (IR) light from the laser 130, as shown in FIG. 1. The laser 130 should, beneficially, be arranged to illuminate the region outside the optical zone. However, it should not be limited to this case, since accurate real-time measurement can be performed even when the laser 130 modifies the optical zone directly, so long as the modification does not result in scattering or other phenomenon that is not consistent with the desired refractive change.

The wavefront aberrometer 110 beneficially communicates with the laser 130 through a hardware or software link (not shown). The wavefront aberrometer 110 provides a feedback signal to the laser 130 for end-point detection and supports the HUD 160. The feedback signal from the wavefront aberrometer 110 may control the progress of the corrective procedure administered by the laser 130 based upon one or more characteristics of the patent's eye measured by the wavefront aberrometer 110. A surgeon can use the HUD 160 to evaluate the progress of the procedure. The wavefront aberrometer 110 may operate in conjunction with the laser 130 to terminate the treatment once a desired correction has been obtained and measured by the wavefront aberrometer 110.

Figure 2:
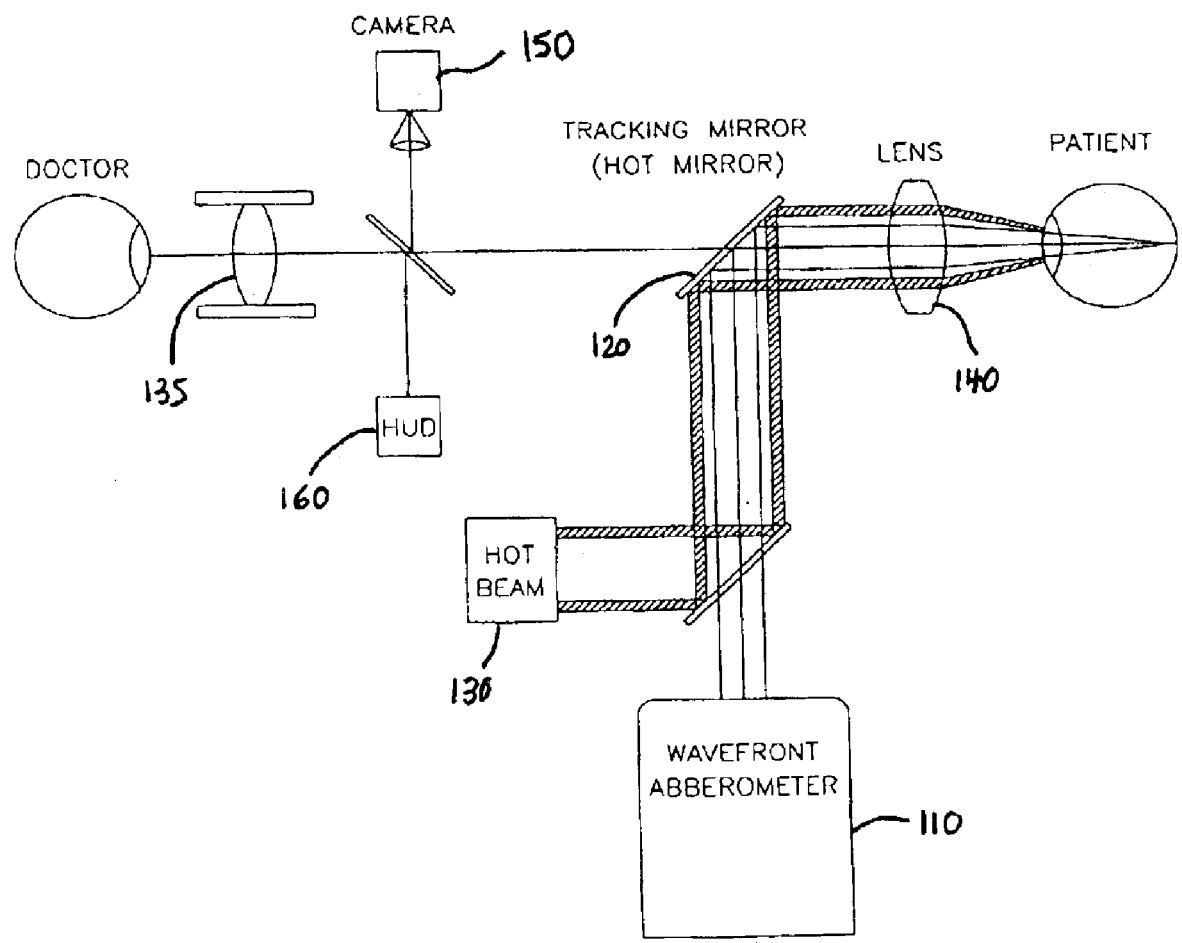
FIG. 2 is a functional block diagram of another embodiment of a laser treatment system including a laser refractive surgery instrument and an objective aberrometer.

FIG. 2 shows a functional diagram of another embodiment of an integrated laser treatment system 100, comprising a laser refractive surgery instrument that is integrated with a wavefront aberrometry system. The major difference between the embodiments of FIG. 1 and FIG. 2 is that the embodiment of FIG. 2 includes a tracking mirror which allows both the laser 130 and the wavefront aberrometer 110 to track movements of a patient's eye during a procedure. Again, a feedback signal from the wavefront aberrometer 110 may control the progress of the corrective procedure administered by the laser 130 based upon one or more characteristics of the patent's eye measured by the wavefront aberrometer 110.

Figure 3:
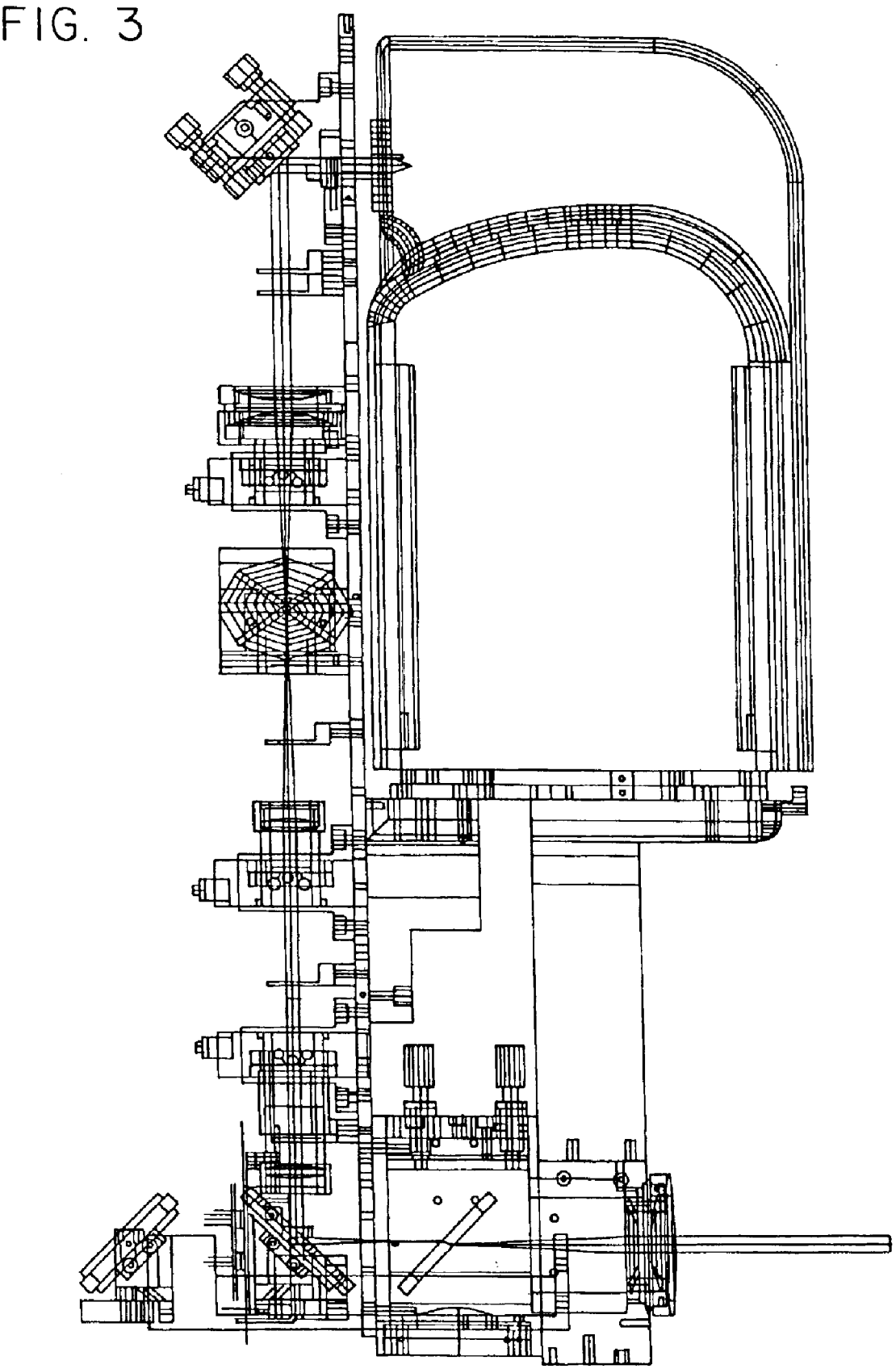
FIG. 3 shows a structural diagram of a laser treatment system including a laser refractive surgery instrument and an objective aberrometer.

FIG. 3 shows a structural configuration of a laser treatment system including a laser refractive surgery instrument and an objective aberrometer, such as an embodiment having the functional diagram of FIG. 1.

A goal of the wavefront measurement is to monitor the change in the spherical value of the eye during the corrective procedure. It is important that measurement not be confused by changes in the accommodative state of the crystalline lens in the patient's eye. In the case of the making a hyperopic patient more emmetropic, the change in the sphere value will tend to make the target more blurry during the treatment. In the case of making a myopic patient more emmetropic, the change in sphere will tend to make a fogged target clear. Once the target becomes clear, the accommodation of the eye would tend to follow the target. Then large changes in the corneal shape could occur while the wavefront aberrometer 110 shows no change in the sphere value. To prevent either of these outcomes, the eye target can be moved during the treatment to maintain the presentation of a fogged eye target to the patient. This movement can be controlled by inputs from wavefront sensor, by predictions from the treatment nomogram, or by inputs from other measurements of the patient's accommodative state.

It is possible to monitor the accommodative state of the patient's eye by several means. For instance, a camera can be located conjugate to the position of the fogged target of the eye. When the target intensity is very bright, the fogged eye target can be viewed on the retina through the eye lens. If the target becomes clearer, the eye is not longer focused at infinity but instead is focusing on the target. A more practical system results if an additional probe beam is added that has a divergence that corresponds to fogged target. A retinal camera will show a small spot when the patient is focused at infinity. The spot size increases as the eye is focused nearer. Additional cameras located a various location on either side of the conjugate location can also be used to measure the accommodative state, with each camera location corresponding to a different distance that the eye is focused. To make a more compact system, a diffractive optic can be made that maps different regions on a single charge coupled device (CCD) camera to different accommodative states. The different beam sizes in the different regions can be evaluated to determine at what range the eye is focused. A compact beam viewed on the retina corresponds to the eye adjusted for far vision as the eye tries to focus on the fogged target. It is also possible to monitor the accommodative state of the eye with a retinal camera that is positioned conjugate to the target in its fogged position and that views the primary injected laser beam. An alternative is to paralyze the accommodative response of the eye by pharmaceuticals.

Figure 4:
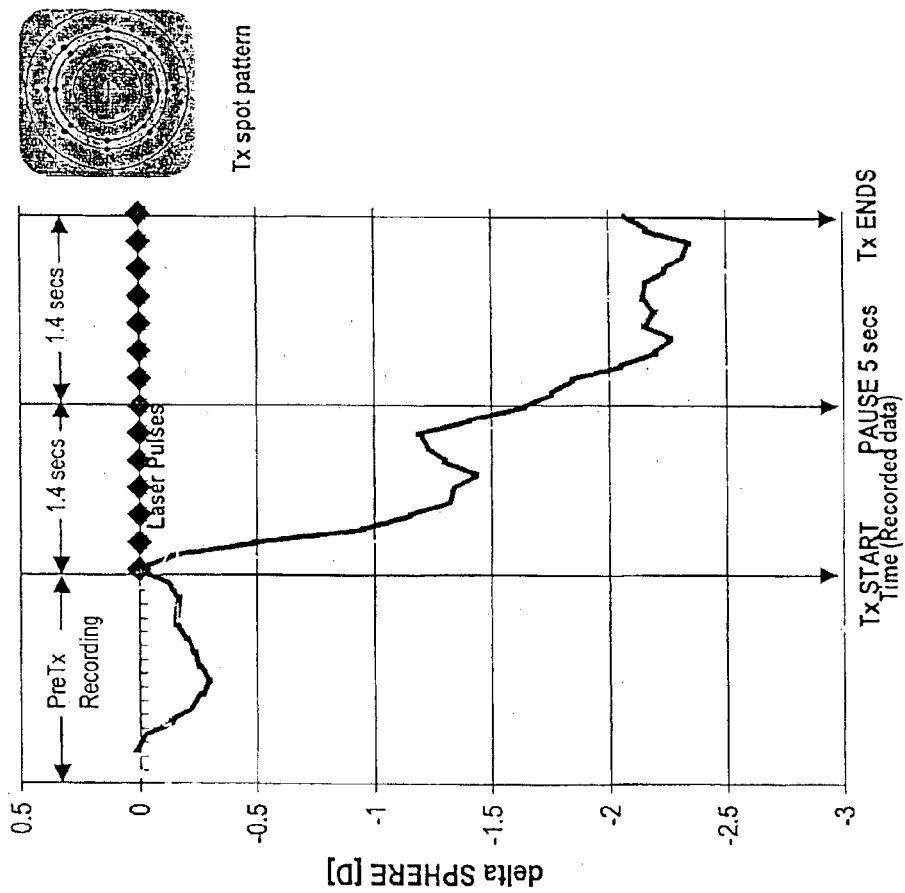
FIG. 4 shows a first example of a real-time measurement from an interactive Wavefront-LTK procedure.
Figure 5:
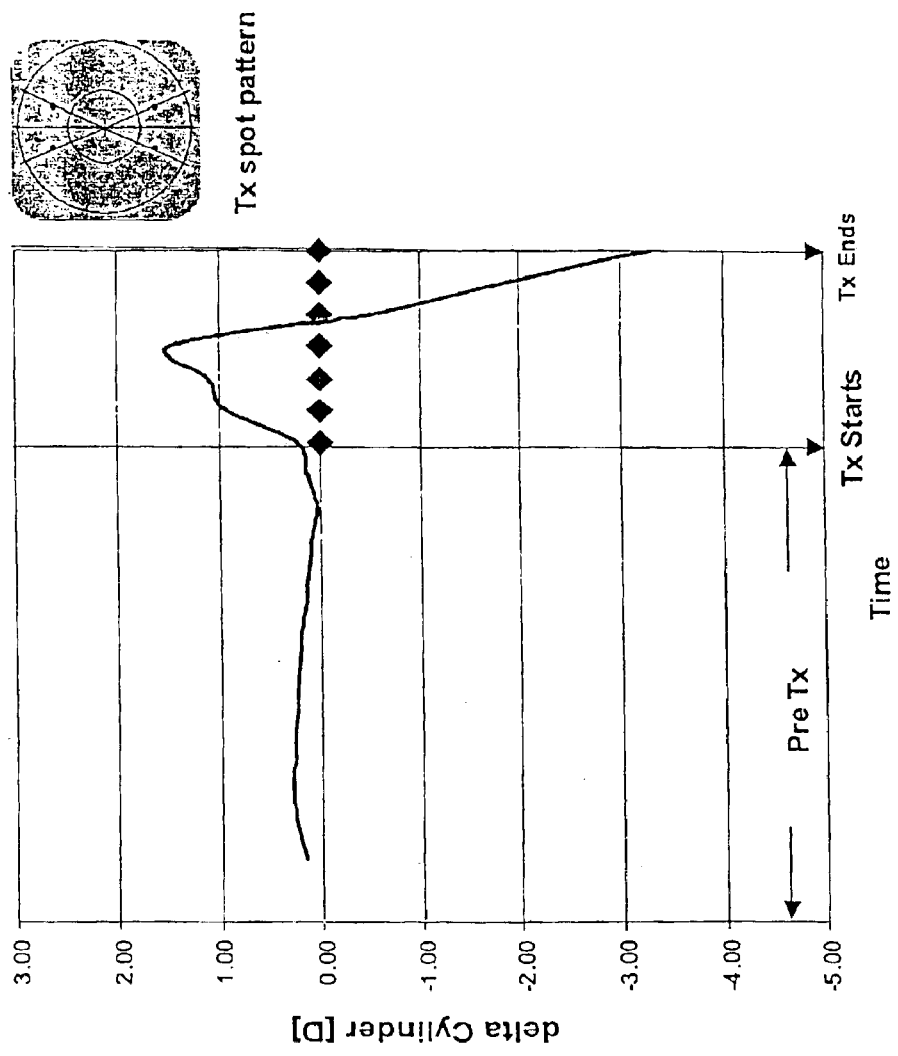
FIG. 5 shows a second example of a real-time measurement from an interactive Wavefront-LTK procedure.

FIGS. 4 and 5 illustrate characteristics obtained from measurements taken by a wavefront aberrometer during LTK procedures using the system of FIG. 3 having the functional diagram of FIG. 1. FIG. 4 illustrates changes to a first patient's eye's spherical characteristics as a series of laser pulses are applied to the eye. A correction of −2.22D is obtained after 14 pulses are applied. If, for example, a correction of only −2.00 was desired, the data provided by the wavefront aberrometer would have indicated that the procedure should be terminated after only 9 pulses. In that case, a feedback control signal from the wavefront aberrometer may operate to shut of the energy source (laser) applying the corrective procedure aft6er the ninth pulse. Meanwhile, FIG. 5 illustrates changes to a second patient's eye's cylindrical characteristics as a series of laser pulses are applied to the eye.

The following are some features that may be provided by a system and method as disclosed herein.

(1) The refractive surgery laser and the diagnostic system are beneficially provided in the same instrument.

(2) A signal may be used for refractive adjustment endpoint detection.

(3) The laser pattern may be adjusted based on information received from the diagnostic instrument (4) The laser exposure may be adjusted based on the information received from the diagnostic instrument.

(5) A higher order aberration may be controlled by a signal from the diagnostic instrument to the laser.

(6) An eye target may be incorporated that the patient views during the treatment.

(7) An eye target may be adjusted to maintain proper patient accommodation state during treatment.

(8) An accommodation state of a patient's eye may be measured during treatment.

(9) Two video cameras may be used to set an angle to the optical axis of eye. When imaged pupils appear at correct places in the cameras, the eye will be at the proper distance from the optical system.

(10) A heads-up display may be included to provide a real-time update of display of the sphere, cylinder and axis. A treating physician may view these values through the oculars when the patient is lined up to the optical system.

(11) An indication may be provided on the heads-up display if the patient is not properly lined up for good wavefront measurements to be performed.

(12) Algorithms and electronics may be provided to synchronize the firing of the pulses of the LTK laser in between sample times of the wavefront aberrometer.

(13) Algorithms and electronics may be provided to move the optical stage of the wavefront aberrometer at optimal times during laser pulses so that the wavefront sensor will have the best measurements and the wavefront sensor will stay in range while the treatment progresses from beginning to end.

(14) Algorithms may be provided to match particular Zernike polynomials to the firing of the pulses of the laser and the influence functions.

(15) An eye tracker may use the video signal of infrared light that fills the pupil as it comes from the eye and appears on a camera that images the iris.

(16) An eye tracker may use the light disk that appears to fill the entire pupil of the eye and is projected onto a high speed quad cell to follow the eye at a kilohertz rate.

(17) An eye tracker arrangement may use a fold mirror such that both the wavefront sensor and the treatment laser follow any small motions of the eye.

(18) A wavefront aberrometer with a wide field of view may be used that can obtain good wavefront measurements even if the tracking mirror only directs the treatment beam and not the wavefront aberrometer field of view.

(19) A small pickoff mirror situated in between the field of view of the two oculars may be used to send the beam to a wavefront aberrometer.

(20) Relay telescopes may be incorporated to image pupil into a wavefront abberometer.

(21) A fixture that acts as a model eye may be automatically inserted and measured by the wavefront aberrometer before each treatment to verify proper operation of the aberrometer before each patient procedure.

(22) A model eye test fixture may be automatically varied to verify proper operation of control loop operation of the aberrometer and treatment laser control system before each patient procedure.

(23) A stabilized laser diode (SLD) illumination beam may be aligned off-center from the optical axis to reduce stray reflections off lenses from coming back onto the wavefront sensor.

(24) A SLD beam may be aligned on the optical axis with polarizing elements used to reduce stray reflections off lenses from coming back onto the wavefront sensor.

(25) Although the above-described embodiments describe correction procedures involving lasers, other energy sources and wavelengths may be employed. For example, it has been discovered that certain corrective procedures (e.g., Presbyopic corrections—both ciliary and lenticular pliancy modifications) may be achieved through the application of ultrasound energy to the eye. In such cases, it is still possible to employ the principles described herein to perform a procedure to modify the refraction of the eye and, while the procedure is being performed, measure the refraction and/or an aberration of the eye, and terminate the procedure when a change the measured refraction and/or the measured aberration reaches a desired value.

(26) An adaptive algorithm may be employed to automate the corrective procedure based upon a feedback signal derived from the wavefront measurements. In that case, an initial wavefront measurement of a patient's eye may be taken prior to the start of corrective procedures. Based upon one or more measured characteristics of the eye, an adaptive algorithm may begin the corrective procedure. A dynamic nomogram may be obtained from real-time sampled wavefront errors measured during the corrective procedure. From the nomogram, a minimized aberration profile endpoint may be determined during the corrective procedure.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

What is claimed is:

1. A system for adjusting an optical characteristic of an eye, comprising:
   a refractive surgery instrument adapted to perform a procedure to modify refraction of an eye;
   an objective diagnostic apparatus adapted to measure at least one of the refraction of the eye and an aberration of the eye concurrently with the procedure being performed; and
   an aperture-sharing element adapted to inject a refractive surgery beam and a monitoring diagnostic beam into the eye.

2. The system of claim 1, wherein the objective diagnostic apparatus is adapted to provide a control signal to the laser refractive surgery instrument for controlling the procedure.

3. The system of claim 1, further comprising a display adapted to display at least one characteristic of the eye measured by the objective diagnostic apparatus.

4. The system of claim 1, wherein the objective diagnostic apparatus includes a wavefront aberrometer.

5. The system of claim 1, wherein the aperture-sharing element includes a dichroic mirror.

6. The system of claim 1, wherein the aperture-sharing element includes a tracking mirror.

7. The system of claim 1 wherein the aperture-sharing element is adapted to simultaneously inject the refractive surgery beam and the monitoring diagnostic beam into the eye.

8. A method of adjusting a refraction of an eye, comprising:
   performing a procedure to modify the refraction of the eye;
   concurrently with the procedure being performed, measuring at least one of the refraction of the eye and an aberration of the eye; and
   terminating the procedure when a change in at least one of the measured refraction and the measured aberration reaches a desired value.

9. The method of claim 8, wherein the procedure to modify the refraction of the eye is a Laser Thermal Keratotomy procedure.

10. The method of claim 8, wherein the procedure to modify the refraction of the eye is a Laser Thermal Drying procedure.

11. The method of claim 8, measuring the refraction and/or an aberration of the eye includes employing a wavefront aberrometer.

12. The method of claim 8, further comprising displaying at least one characteristic of the eye measured by the objective diagnostic apparatus.

13. The method of claim 8, wherein performing the procedure to modify the refraction of the eye comprises injecting a refractive surgery beam into the eye.

14. The method of claim 13, wherein measuring the refraction and/or an aberration of the eye comprises injecting a monitoring diagnostic beam into the eye simultaneously with injecting the refractive surgery beam into the eye.

* * * * *